United States Patent [19]

Hirakawa et al.

[11] 4,411,991

[45] Oct. 25, 1983

[54] PROCESS FOR FERMENTATIVE PRODUCTION OF AMINO ACIDS

[75] Inventors: Kan Hirakawa, Takasago; Ryoji Takakuma, Kakogawa; Koji Nomura, Takasago; Masami Katoh; Kiyoshi Watanabe, both of Akashi, all of Japan

[73] Assignee: Kanegafuchi Chemical Industry Company, Limited, Osaka, Japan

[21] Appl. No.: 302,996

[22] Filed: Sep. 17, 1981

[30] Foreign Application Priority Data

Oct. 7, 1980 [JP] Japan .............................. 55-140818
Apr. 9, 1981 [JP] Japan .............................. 56-54127
Apr. 21, 1981 [JP] Japan .............................. 56-60098
Jun. 16, 1981 [JP] Japan .............................. 56-93130

[51] Int. Cl.$^3$ .................... C12P 39/00; C12P 13/04; C12P 13/22; C12P 13/20; C12P 13/14; C12P 13/08; C12P 13/06; C12R 1/13; C12R 1/15; C12R 1/225; C12R 1/285; C12R 1/365; C12R 1/46

[52] U.S. Cl. .................................. 435/42; 435/106; 435/108; 435/109; 435/110; 435/115; 435/116; 435/840; 435/843; 435/853; 435/862; 435/872; 435/885; 426/43

[58] Field of Search .................. 435/42, 106, 108–112, 435/115, 116; 426/42, 43

[56] References Cited

U.S. PATENT DOCUMENTS 1,932,755 10/1933 Stiles et al. .............................. 435/42
3,655,510 4/1972 Tanaka et al. .................. 435/115 X
4,013,508 3/1977 Zangrandi et al. .............. 435/109 X

*Primary Examiner*—Lionel M. Shapiro
*Attorney, Agent, or Firm*—Armstrong, Nikaido, Marmelstein & Kubovcik

[57] ABSTRACT

A process is disclosed in which an amino acid-producing microorganism having an ability to assimilate lactic acid is aerobically cultivated in the presence of at least one lactic acid microorganism in an aqueous nutrient medium containing at least one carbohydrate which is assimilable by the lactic acid microorganism but nonassimilable or weakly assimilable by the amino acid-producing microorganism as the main carbon source and an accumulated amino acid is recovered from the culture broth. An industrially advantageous production of an amino acid has become feasible by utilizing inexpensive carbon sources or those organic substances in agricultural or livestock wastes that have heretofore not been effectively utilized.

18 Claims, No Drawings

PROCESS FOR FERMENTATIVE PRODUCTION OF AMINO ACIDS

BRIEF SUMMARY OF THE INVENTION

The present invention relates to a process for fermentative production of amino acids. More specifically, the present invention relates to a process in which an amino acid-producing microorganism having an ability to assimilate lactic acid is aerobically cultivated in the presence of at least one lactic acid microorganism in an aqueous nutrient medium containing at least one carbohydrate which is assimilable by the lactic acid microorganism but nonassimilable or weakly assimilable by the amino acid-producing microorganism and an accumulated amino acid is recovered from the culture broth.

An object of the present invention is to provide an industrially advantageous process for production of amino acids which are important to human and animal nutrition by utilizing inexpensive carbon sources or those organic substances in agricultural or livestock wastes that have heretofore not been effectively utilized.

Another object of the present invention is to reduce environmental pollution caused by agricultural and livestock wastes.

Finiteness of natural resources has recently been recognized and their effective utilization has become current topics, but effective utilization of the resources is still in its infancy. For instance, it was pointed out in an FAO study that, of 74 million tons of whey produced in the world in 1973, only half of this amount was used mainly as feed for livestock and the rest wasted. This means that more than 2 million tons of lactose and more than 300 thousand tons of valuable proteins were wasted in the year because wheys discharged from cheese or casein factories contain about 5% lactose and about 1% proteins. This situation not only causes loss of natural resources but also creates a serious disposal problem from the standpoint of pollution; thus, there has been long-felt need for better processes for utilization of whey. The continued efforts by the dairy industry over the last decade, however, have failed to provide a satisfactory answer to the problem. One of the extensively explored approaches has been the fermentative utilization of whey. For instance, the conversion of whey solids to an edible yeast cell mass was attempted using a strain of yeast capable of assimilating lactose (U.S. Pat. No. 3,818,109). The extensive use of whey as a starting material for fermentation, however, has not yet been successful.

This is conceivably ascribable to the limited presence of microorganisms capable of assimilating lactose contained in whey.

An ability to assimilate carbon sources such as carbohydrates is an important characteristic for taxonomy or identification of microorganisms. It is quite difficult or impossible to impart the assimilability to microorganisms or enhance the assimilability of microorganisms by conventional artificial mutation techniques.

Accordingly, in known fermentative process for production of amino acids in which a single strain of a microorganism is employed (mono-culture method), utilizable starting materials are limited to those which can be effectively assimilated or metabolized by the adopted strain and productivity is governed by those fundamental genetic properties possessed by the strain which can hardly be improved by artificial mutation. On the other hand, genetic engineering techniques have recently become promising as a technique for creation of mutant strains of microorganisms; nevertheless, adoption of the technique on an industrial scale still awaits resolution of many problems such as confirmation of the stability and safety of recombinant strains.

According to the process of the present invention, amino acids can fermentatively be produced by the use of carbon sources nonassimilable or weakly assimilable by amino acid-producing microorganisms by cultivating amino acid-producing microorganisms in the presence of lactic acid microorganisms which have been employed from old times for production of food and drink; thus, the present invention permits extensive utilization of starting materials according to the assimilating abilities of the employed lactic acid microorganisms. In other words, the present invention, by a safe and simple technique, has attained the same effects as might be attained by genetic engineering, wherein genetic properties of lactic acid microorganisms are imparted to amino acid-producing organisms, although no genetic engineering techniques are adopted or utilized in the present invention.

There have been some reports on a method of mixed-cultivation; David E. F. Harrison considered the scope and possibilities of application of mixed-cultivation to industrial fermentation [Adv. Appl. Microbiol., Vol. 24, p129 (1978)]. On production of amino acids by mixed populations of microorganisms, M. Suzuki and S. Yamatodani reported that L-glutamic acid was produced in large amounts by mixed-cultivation of *Escherichia coli* (E) and a strain of Corynebacterium (A); as the mechanism, they showed that α-ketoglutarate is accumulated by the E-strain and the α-ketoglutarate is in turn aminated by the A-strain to produce L-glutamate. In this process, the E-strain must have an ability to produce α-ketoglutarate, a precursor of glutamic acid, which fact substantially differing from the present invention [M. Suzuki and S. Yamatodani; Annual Meat. Agr. Chem. Soc. Jpn., Abst., p.164 (1967)]. There is also known a process for producing L-lysine in which a hydrocarbon-assimilating microorganism belonging to the genus Arthrobacter or Brevibacterium and a L-lysine-producing microorganism belonging to the genus Corynebacterium are mix-cultivated in a nutrient medium containing a hydrocarbon as the main carbon source (U.S. Pat. No. 3,655,510). A method is also known in which single cell proteins are obtained by mix-cultivating a yeast belonging to the genus Saccharomyces or Candida and a lactic acid-producing microorganism belonging to the genus Lactobacillus (U.S. Pat. No. 3,818,109, Ger. Offen. No. 2,403,306, Ger. Offen. No. 2,500,323).

Thus, although attempts have so far been made to produce a variety of fermentative products by mixed-cultivation, an industrially advantageous production of amino acids by a mixed-cultivation of a lactic acid microorganism and an amino acid-producing microorganism is unknown.

On the other hand, it is already known that an amino acid is accumulated in a nutrient medium by aerobic cultivation of an amino acid-producing microorganism in a nutrient medium containing lactic acid as the main carbon source [for example, V. N. Shaposhnikov and V. S. Isaeva, Mikrobiologia Vol 36, p31 (1967), K. Seto and T. Harada, T. Ferment. Technol., Vol 47, p558 (1969)]. Lactic acid, however, has rarely been employed as a starting material for industrial production of amino acids because extraction and purification of lactic acid from a culture broth of lactic acid fermentation are difficult and a lactic acid obtained by synthesis is costly. Two-step fermentation is conceivable in which lactic acid fermentation and an amino acid fermentation is combined serially, but this method requires an alkaline substance such as calcium carbonate or ammonia as a neutralizing reagent and takes a long period of time since the rate of lactic acid production is slowed down by the inhibition of the fermentation due to the product, lactic acid, accumulated in high concentrations. Moreover, the second step of this method requires addition of an acidic substance for the regulation of an increase in a pH attendant on consumption of lactic acid.

In the process of the present invention, however, lactic acid produced by lactic acid microorganisms is presumed to be promptly utilized by amino acid-producing microorganisms, with the result that the starting carbohydrate can be converted into amino acids in one step operation; thus, efficient fermentative production of amino acids can be carried out, and at the same time, the amount of the neutralizing reagent can be minimized and extration and purification of amino acids from the resulting culture broth can be facilitated.

The present invention is a process for producing an amino acid which comprises aerobically cultivating an amino acid-producing microorganism having an ability to assimilate lactic acid in the presence of at least one lactic acid microorganism in an aqueous nutrient medium containing at least one carbohydrate which is assimilable by the lactic acid microorganism but nonassimilable or weakly assimilable by the amino acid-producing microorganism as the main carbon source, accumulating an amino acid in the resulting culture broth, and recovering the amino acid from the culture broth.

Amino acids produced by the process of the present invention are, for example, L-lysine, L-valine, L-threonine, L-glutamic acid, L-isoleucine, L-leucine, DL-alanine, L-phenylalanine, L-tyrosine, L-tryptophane, L-arginine, L-histidine, L-serine, L-glycine, and L-aspartic acid.

DETAILED DESCRIPTION OF THE INVENTION

Although the mechanism of the process of the present invention has yet to be clarified, a mechanism is conceivable through which metabolites containing lactic acid as the main ingredient are produced from a carbohydrate by a lactic acid microorganism and then assimilated by an amino acid-producing microorganism to be converted into an amino acid. In other words, a system is conceivable in which the first microorganism—a lactic acid microorganism (L)—is in charge of glycolysis of a carbohydrate and the second microorganism—an amino acid-producing microorganism (A)—is in charge of amino acid production from those metabolites containing lactic acid as the main ingredient that are produced by the first microorganism. Since oxydation of lactic acid conceivably occurs through the main pathway in which lactate dehydrogenase (LDH) is involved, amino acids are presumably produced by this enzyme via pyruvic acid which is situated in the center of a metabolic pathway of general microorganisms as shown below.

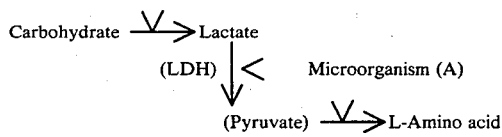

A hypothetical mechanism for L-amino acid production from a carbohydrate in the present invention A distinctive feature of the present invention is that simple combination of the two systems of microorganisms not only conveniently utilizes characteristics of the two microorganisms but also presumably produces an unknown synergism, and therefore several industrially advantageous effects can be expected which cannot be had by a mono-culture.

Advantages of the present invention will be explained below.

First, organic substances which had been unusable as a starting material for fermentation owing to their nonassimilability or weak assimilability by amino acid-producing microorganisms have come to be utilized as a starting material for amino acid fermentation. For instance, cheese whey or casein whey discharged from factories can be utilized as a suitable starting material in the process of the present invention. It goes without saying that it is industrially very advantageous that inexpensive starting materials can be utilized according to availability of starting materials.

Second, the present invention contributes to reduce environmental pollution because organic substances contained in whey, or liquid wastes or refuses from starch factories are converted into amino acids and microbial cells by their utilization as a starting material for fermentation, with the result that BOD components which are causes of pollution are greatly reduced through processes for recovering amino acids.

Third, fermentative productivity is improved conspicuously as compared with mono-culture methods. When an amino acid-producing microorganism having a high ability to assimilate lactic acid is employed, the consuming rate of a carbohydrate as a substrate, which rate is often proportional to the rate of product formation, depends on the activity of a lactic acid microorganism, that is, the rate of lactic acid fermentation. In a system of mixed-cultivation of the present invention, lactic acid produced and accumulated by lactic acid microorganisms is rapidly utilized by amino acid-producing microorganisms, with the result that there is presumably produced the same effect as that of dialysis fermentation, which accelerates fermentation by removal of products through a membrane; consequently, the high activity of lactic acid microorganisms is maintained. Presumably, there is also a possibility that the high rate of lactic acid fermentation is maintained by an unknown synergistic effect such as an accelerating effect due to decomposition of hydrogen peroxide, which is likely to cause inhibition of metabolism, by catalase which is lacking in lactic acid microorganisms but provided by amino acid-producing microorganisms. When homofermentative lactic acid microorganisms, which produce only lactic acid from carbohydrates, are employed, it probably contributes to high productivity that the conversion rate of a carbohydrate into lactic acid reaches as high as 90~100% resulting in reduced loss of the carbon source.

The present inventors have observed that lactic acid fermentation, although generally carried out under anaerobic conditions, can be effectively conducted in the process of the present invention even under aerobic conditions generally required for amino acid fermentation; this finding underlies the foregoing speculations.

Fourth, the advantage of the present invention resides in resistance to contamination by foreign microorganisms. The David E. F. Harrison's review referred to hereinbefore cites resistance to contamination by foreign microorganisms as an advantage of mixed-cultivation. In the process of the present invention in which lactic acid microorganisms are employed, besides the mechanism explained by the author, antimicrobial substances (for instance, nisin by *Streptococcus lactis* and diplococcin by *Streptococcus cremoris*, etc.) are presumably involved in minimizing effects of contamination by foreign microorganisms. Prevention of contamination by foreign microorganisms is one of the most important problems posed in industrial fermentation.

Amino acid-producing microorganisms, having an ability to assimilate lactic acid, employed in the process of the present invention is a member belonging to a genus selected from the group consisting of Alkaligenus, Acinetobacter, Arthrobacter, Bacillus, Brevibacterium, Corynebacterium, Flavobacterium, Micrococcus, Microbacterium, Nocardia, Proteus, Serratia, Candida, Saccharomyces, Sporoboromyces, and Schizosaccharomyces.

The ability of amino acid-producing microorganisms to assimilate lactic acid can be checked and compared by aerobically cultivating a test microorganism in a minimum medium containing lactic acid (L- or DL-lactate) as a single carbon source followed by observing the growth of the microorganism. It is also possible to isolate strains having an excellent ability to assimilate lactic acid from nature by an enrichment culture using a minimum medium containing lactic acid (0.5~2%).

Representative examples of strains exployed in the process of the present invention as amino acid-producing microorganisms are as follows:

| | |
|---|---|
| *Alkaligenes faecalis* | IFO-3160 |
| *Alkaligenes marshallii* | ATCC-21030 |
| *Acinetobacter sp-38-15* | FERM-P-2187 |
| *Acinetobacter calcoaceticus* | IFO-12552 |
| *Arthrobacter paraffineus* | ATCC-15591 |
| *Arthrobacter citreus* | ATCC-17775 |
| *Arthrobacter sp-18* | FERM-P-1481 |
| *Bacillus circulans* | IFO-3329 |
| *Bacillus megatherium* | IFO-3970 |
| *Bacillius subtilis* | IAM-1071 |
| *Brevibacterium ammoniagenes* | ATCC-19350 |
| *Brevibacterium acetylicum* | IAM-1790 |
| *Brevibacterium thiogenitalis* | IFO-12400 |
| *Brevibacterium flavum* | ATCC-13826 |
| *Brevibacterium lactofermentum* | ATCC-13869 |
| *Corynebacterium hydrocarboclastum* | ATCC-15960 |
| *Corynebacterium acetoacidophilum* | ATCC-13870 |
| *Corynebacterium glutamicum* | ATCC-13032 |
| *Flavobacterium lutescens* | IFO-3085 |
| *Micrococcus luteus* | IFO-3333 |
| *Micrococcus roseus* | IFO-3764 |
| *Microbacterium ammoniafilm* | ATCC-15354 |
| *Nocardia alkanoglutinosa* | ATCC-31220 |
| *Nocardia erythropolis* | IAM-12122 |
| *Norcardia lyena* | ATCC-21338 |
| *Proteus morganii* | IFO-3848 |
| *Serratia marcescens* | IFO-3054 |

-continued

| | |
|---|---|
| *Serratia plymuthium* | IFO-3055 |
| *Saccharomyces oviformis* | IAM-4325 |
| *Saccharomyces cerevisiae* | IFO-0971 |
| *Candida humicola* | IFO-1577 |
| *Candida lypolitica* | IFO-0746 |
| *Sporoboromyces roseus* | IFO-1037 |
| *Schizosaccharomyces pombe* | IFO-6170 |

(Note)
IAM: Institute of Applied Microbiology, Univ. of Tokyo, 1-chome, Yayoi, Bunkyo-ku, Tokyo, Japan
IFO: Institute for Fermentation, Osaka, Juso, Nishinomachi, Higashiyodogawa-ku, Osaka, Japan
FERM-P: Fermentation Research Institute, Agency of Industrial Science and Technology, the Ministry of Industrial Trade and Industry, Chiba-city, Japan These strains have an ability to assimilate lactic acid but the intensity of the assimilability differ with different strains. It is also possible to induce or enhance the assimilability by aerobic cultivation of an amino acid-producing microorganism in a medium containing 0.2~4% by weight/volume of lactic acid (sodium or calcium lactate). It is known that, of lactate dehydrogenases which presumably govern the rate-limiting step of lactate utilization, L(+)-lactate dehydrogenase can be induced by aerobic cultivation of a microorganism in the presence of a lactate [Ellen I. Carvie; Microbiological Review, Vol 44(1), p106~139 (1980)]. Artificial mutation can also enhance the lactic acid assimilability.

From among the microorganisms listed above as examples, strains having high amino acid productivity can be obtained by the usual mutation treatment such as those using chemical mutagenic agents, for example, N-methyl-N'-nitro-N-nitrosoguanidine (NTG), or radiation, for example, ultraviolet rays and X-rays followed by isolation of mutant strains according to known methods [K. Nakayama, et al., J. Gen. Appl. Microbiol., Vol 7, p41 (1961); Koichi Yamada, Biotechnol. and Bioeng., Vol 19, p1563 (1977)].

L-Lysine-producing strains are, for example, as follows:

auxotrophs requiring homoserine (or threonine plus methionine [U.S. Pat. No. 2,979,439, British Pat. No. 1,200,587]: auxotrophs requiring any one of the following amino acids; threonine, isoleucine, valine, methionine, leucine, alanine, arginine, histidine, phenylalanine, cystine, cysteine [French Pat. No. 1,486,235, French Pat. No. 158,154, U.S. Pat. No. 3,527,672, British Pat. No. 1,184,530, British Pat. No. 1,118,719]; mutants derived from an auxotroph requiring homoserine [U.S. Pat. No. 3,524,797, British Pat. No. 1,186,988, Belgian Pat. No. 753,394); mutants resistant to L-lysine analogues such as S-(2-aminoethyl)-L-cysteine (S-AEC) [U.S. Pat. No. 3,707,441; K. Sano and I. Shiio: J. Gen. Appl. Microbiol., Vol 16, p373 (1970); E. Takenouchi et al., Agr. Biol. Chem., Vol 41,615 (1977); U.S. Pat. No. 4,123,329]; mutants sensitive to threonine or methionine [French Pat. No. 1,200,353; I. Shiio and R. Miyajima, J. Gen. Appl. Mcrobiol., Vol 15, 267 (1969)].

L-Valine-producing strains are, for example, as follows:

auxotrophs requiring (1) isoleucine, (2) leucine, (3) threonine, (4) homoserine, or threonine plus methionine, or (5) arginine [R. Ishii et al., J. Gen. Appl. Microbiol., Vol 13, p217 (1967); U.S. Pat. No. 3,700,556]; mutants resistant to α-aminobutyrate or 2-thiazoleala-nine [M. Kisumi, J. Bacteriol., Vol 106, p493 (1971); Japanese patent second publication No. 44877/1973 and No. 68794/1973].

L-Threonine-producing strains are, for example, as follows:

auxotrophs requiring one or more of the following amino acids: methione, isoleucine, lysine, diaminopimelic acid (French Pat. No. 1,489,910; British Pat. No. 1,190,687; French Pat. No. 1,591,232; West-German Pat. No. 1,817,666); mutants resistant to L-threonine analogues such as α-amino-β-hydroxyvaleric acid (AHV) (U.S. Pat. No. 3,582,471).

L-Glutamic acid-producing strains are, besides ones listed hereinbefore as examples, as follows:

mutants requiring glycerol [Y. Nakano et al., Agr. Biol. Chem., Vol 34, 1875 (1970)]; mutants requiring oleic acid [Okazaki et al., Agr. Biol. Chem., Vol 31, p1314 (1967)].

L-Isoleucine-producing strains are, for example, as follows:

mutants resistant to L-isoleucine analogues, α-AHV, α-aminobutyric acid, or isoleucine hydroxamate.

L-Leucine-producing strains are, for example, as follows:

auxotrophs requiring L-isoleucine or α-aminobutyrate [R. Ishii et al., J. Gen. Appl. Microbiol., Vol 13, p217 (1967); F. Yoshinaga et al., ibid., Vol 13, p25 (1967)]; mutants resistant to 2-thiazolealanine [T. Tsuchida et al., Agr. Biol. Chem., Vol 38, 1907 (1974)] or leucine analogues [R. A. Calvo and J. M. Calvo, Science, Vol 156, 1107 (1967)].

L-Tyrosine-producing strains are, for example, as follows:

auxotrophs requiring L-phenylalanine [K. Nakayama et. al., J. Agr. Chem. Soc. Jpn., Vol 35, p142 (1961)]; mutants resistant to 5-methyltryptophane [I. Shiio et al., Agr. Biol. Chem., Vol 36, p2315 (1973)].

L-Tryptophane-producing strains are, for example, as follows:

mutants resistant to 5-methyltryptophane (Japanese patent second publication Nos. 18,828/1973 and 39517/1978); auxotrophs requiring L-tyrosine and L-phenylalanine [H. Hagino et al., Agr. Biol. Chem., Vol 39, p343 (1975)].

Addition of anthranilic acid or indole, a precursor of L-tryptophane biosynthesis, to the fermentation medium during the cultivation is effective in improving the yield of L-tryptophane production.

L-Phenylalanine-producing strains are, for example, as follows:

auxotrophs requiring L-tyrosine (U.S. Pat. No. 3,759,790); mutants resistant to p-fluorophenylalanine [S. Sugimoto et al., Agr. Biol. Chem., Vol 37, p2327 (1973)].

L-Arginine-producing strains are, for example, as follows:

mutants resistant to arginine hydroxamate or 2-thiazolealanine [M. Kizumi et al., Appl. Microbiol., Vol 22, p987 (1971); K. Nakayama and H. Yoshida, Agr. Biol. Chem., Vol 36, p1675 (1972); K. Kubota et al., J. Gen. Appl. Microbiol., Vol 19, p339 (1973)].

Lactic acid microorganisms employed in the process of the present invention include bacteria which are often called collectively "lactic acid bacteria" and microorganisms belonging to the genus Rhizopus which is a kind of fungi; they belong, for example, to the genus Lactobacillus, Streptococcus, Leuconostoc, Pediococcus, Tetracoccus, Bacillus, and Rhizopus.

Representative examples of lactic acid microorganisms are as follows:

| | |
|---|---|
| Lactobacillus bulgaricus | IFO-3533 |
| Lactobacillus casei | IFO-12004 |
| Lactobacillus acidophilus | IFO-3532 |
| Lactobacillus japonicus | IAM-10068 |
| Lactobacillus thermophilus | IFO-3863 |
| Lactobacillus plantarum | IFO-12006 |
| Lactobacillus delbrueckii | IFO-3534 |
| Lactobacillus pentosus | IFO-4758 |
| Streptococcus cremoris | IFO-3427 |
| Streptococcus thermophilus | IFO-3535 |
| Streptococcus lactis | IFO-12007 |
| Leuconostoc dextranicum | IFO-3347 |
| Pediococcus acidilactici | IFO-3884 |
| Pediococcus pentosaceus | IFO-3891 |
| Pediococcus soyae | IFO-12172 |
| Tetracoccus soyae | ATCC-21787 |
| Bacillus coagulans | IFO-3887 |
| Bacillus laevolactici | ATCC-23492 |
| Rhizopus oryzae | IFO-4706 |

In the process of the present invention, lactic acid microorganisms can be employed singly or in a combination of at least the two. For instance, symbiosis is known to exist between *Lactobacillus bulgaricus* and *Streptococcus thermophilus*, and hence the combination is effective also in the process of the present invention. Lactic acid microorganisms are classified into two groups, that is, homofermentative microorganisms which produce only lactic acid from carbohydrates and heterofermentative microorganisms which produce carbon dioxide, an acetate, and/or ethanol from carbohydrates; homofermentative microorganisms are preferable in the process of the present invention. When the heterofermentative microorganisms are employed in the present invention, presumably an acetate and ethanol which are produced are also utilized by amino acid-producing microorganisms besides lactic acid produced; in this case, however, carbon dioxide, which is one of the metabolites, represents a loss in carbon sources.

Those strains resistant to antibiotics or amino acid analogues which are obtained by subjecting the foregoing lactic acid microorganisms to mutagenic treatments can also be employed in the process of the present invention. For example, in L-lysine production according to the process of the present invention, there can be employed those strains resistant to S-AEC, a L-lysine analogue, which is obtained by mutagenically treating lactic acid microorganisms employed for L-lysine production. As lactic acid microorganisms employed for L-threonine production, there can be employed strains (resistant strains) capable of growing in the presence of S-AEC and L-threonine or strains resistant to α-AHV, a L-threonine analogue. Effective production of L-glutamic acid is made possible by employing lactic acid microorganisms resistant to antibiotics, such as penicillins, or drugs which are added to the culture medium. These strains resistant to drugs can readily be produced by a person skilled in the art.

When such lactic acid microorganism producing an anti-microbial substance as *Streptococcus lactis* and *Streptococcus cremoris* is employed, an amino acid-producing microorganism to be employed in combination is preferably resistant to the antimicrobial substance. To obtain the amino acid-producing resistant mutant strain, an amino acid-producing strain is subjected to the usual mutagenic treatments followed by recovering a strain which can grow in a medium (liquid or solid) containing a culture broth of the lactic acid microorganism producing an antimicrobial substance (the culture broth of the lactic acid microorganism is used as it is because sterilization thereof by heating can inactivate the antimicrobial substance); this method can be advantageous in that contamination by foreign microorganisms is prevented.

The process of the present invention, a process for fermentative production of amino acids, will next be explained in detail.

Procedures for seed cultures will first be described.

One or more strains of lactic acid microorganisms are inoculated into a nutrient medium for lactic acid fermentation containing a sugar such as glucose, fructose, sucrose, lactose, etc.; or molasses, whey, or starch hydrolysates containing these sugars; together with an organic nitrogen source such as yeast extract, corn steep liquor (C.S.L.), and peptone, and cultivated at 25~55° C. For instance, a nutrient medium containing yeast extract and/or C.S.L. in addition to cheese or casein whey is utilized as a suitable medium. The cultivation is usually carried out anaerobically such as by stationary culture, but aerobic culture may also be adopted. Culture broth thus obtained is used as the first seed culture.

It is also possible to use microbial cells obtained by the lactic acid fermentation after they are immobilized in or on a supporting material such as gel-inducing reagents, for example, carrageenan, calcium arginate, and polyacrylamide. The immobilized whole cells can be re-used after being collected by filtration upon completion of fermentation.

On the other hand, seed culture of amino acid-producing strains is prepared as the second seed culture as follows:

Although the usual nutrient medium for cultivating microorganisms can also be used as a culture medium, the seed culture obtained by aerobically cultivating an amino acid-producing microorganism in a nutrient medium containing 0.2~5% (W/V) of lactic acid (L or DL) or its salts permits effective production of amino acids.

As a nutrient medium for preparation of the second seed culture, there can also suitably be used a nutrient medium prepared by adjusting a culture broth obtained by fermentation (usually anaerobic) of lactic acid microorganisms to be employed for amino acid fermentation to attain a lactic acid concentration of 0.2~5% (preferably 0.5~2%) W/V, followed by supplementation with carbon sources such as carbohydrates and alcohols, inorganic salts, organic or inorganic nitrogen sources and so forth. The pH during the cultivation is 5.5~8.0.

The two kinds of seed cultures thus obtained are inoculated into a fermentation medium for amino acid production.

The ratio between the amounts of the seed cultures to be inoculated, although not limited in particular, is usually 10 (volume) of amino acid-producing microorganisms to 0.1~10 (volume) of lactic acid microorganisms. When an amino acid-producing microorganisms has a relatively low ability to assimilate lactic acid, the amount of lactic acid microorganism to be inoculated should be small in order to balance lactic acid production and lactic acid assimilation against each other for effective progress of amino acid fermentation. For instance, when the inoculated amount of a lactic acid microorganism is too large, lactic acid fermentation proceeds so rapidly that lactic acid production and the assimilation rate become unbalanced, with the result that the fermentation leans toward lactic acid production and hence amino acid production drops.

The two kinds of seed cultures are usually inoculated at the same time, but it is also possible to defer inoculation of either of the two. For instance, a lactic acid microorganism is inoculated into the medium after an amino acid-producing microorganism has been aerobically precultivated for a given period (e.g., 2~20 hr) in a nutrient medium containing small amounts (e.g., 0.5~2.0 g/dl) of supplementary carbon sources assimilable by the amino acid-producing microorganism in addition to the main carbon source. The ability of an amino acid-producing microorganism to assimilate lactic acid can be induced for stable fermentation by carrying out the precultivation in a nutrient medium containing 0.2~1.0 g/dl of lactic acid as well as the supplementary carbon source. Examples of the supplementary carbon source are sugars such as glucose and fructose, and alcohols such as ethanol.

It is also possible to employ both the lactic acid microorganism and the amino acid-producing microorganism in combination in the stage of the seed cultivation. To cite one example, the two kinds of microorganisms are inoculated into and aerobically cultivated in an aqueous nutrient medium containing 2~5% W/V of a carbohydrate which is to be used as the main carbon source in amino acid production. Fermentation conditions in this case are similar to those in amino acid production described hereinafter. Culture broth containing the two kinds of microorganisms thus obtained is inoculated into a culture medium for amino acid production.

The carbohydrate used as the main carbon source in the process of the present invention is one which is assimilable by at least one lactic acid microorganism but nonassimilable or weakly assimilable by at least one amino acid-producing microorganism which has an ability of assimilating lactic acid and includes glucose, fructose, sucrose, molasses, starch hydrolysates, cellulose hydrolysates, hydrol, lactose, lactose hydrolysates, fruit juice, casein whey, cheese whey, soybean whey, dextrin, and starch.

The foregoing wheys include acid whey, sweet whey, deproteinized whey (UF-permeate) (an ultrafiltration membrane is used for the deproteinization), and demineralized whey.

Two or more of the carbohydrate illustrated above can be used in combination in the process of the present invention.

It is necessary to select the kind of lactic acid microorganism according to the kind of carbohydrate adopted. For instance, *Lactobacillus bulgaricus, Lactobacillus casei, Streptococcus cremoris,* and *streptococcus thermophilus* are suited for lactose or wheys; *Lactobacillus delbrueckii* and *Streptococcus thermophilus* are suited for molasses; *Lactobacillus thermophilus, Lactobacillus japonicus,* and *Rhyzopus oryzae* are each capable of producing lactic acid from starch or dextrine.

When starch or dextrine is used as the carbon source, fermentative production of amino acids can be conducted effectively by adding amylase to the aqueous nutrient medium and preferably employing a lactic acid microorganism having an amylase activity. Suitable amylase to be employed can be obtained, for example, by dissolving commercially available amylase in water followed by filtering the solution through a membrane having the pore size smaller than 0.5μ such as Millipore filter.

Nitrogen sources in the nutrient medium include ammonia water, ammonia gases, urea, and organic or inorganic ammonium salts such as ammonium chloride, ammonium sulfate, ammonium phosphate, ammonium acetate, and ammonium lactate.

Inorganic substances in the nutrient medium include salts of sodium, potassium, manganese, magnesium, calcium, cobalt, nickel, zinc, copper, and iron with hydrochloric, sulfuric, and phosphoric acids.

To the aqueous nutrient medium are added, besides those nutrients such as vitamines and amino acids required for the growth of amino acid-producing microorganisms, yeast extracts, peptone, casein hydrolysates, soybean protein hydrolysates, corn sheep liquor (CSL), whey, or whey hydrolysates, which contain vitamines, amino acids, or nucleic acid-relating substances, for the purpose of accelerating the growth of lactic acid.

For production of glutamic acid from molasses or wheys, addition of chemicals such as penicillins and surface active agents to the aqueous nutrient medium improves the yield of the product [U.S. Pat. No. 3,080,297; K. Takami et al., Agr. Biol. Chem., Vol 27, p858 (1968)]. The chemicals are added during a period of 4~24 hours after the start of the cultivation. In this case, a lactic acid microorganism to be employed is preferably one resistant to the chemicals to be added. Concentrations or methods for addition of nutrients and the chemicals are similar to those in the usual single cultivation of amino acid-producing microorganisms; however, the optimal amount thereof should be determined under conditions of mix-cultivation since metabolism by lactic acid microorganisms may have an influence on them.

The cultivation is carried out under aerobic conditions of shaking culture or aeration with stirring, etc.

The pH during the cultivation is preferably adjusted to 4.5~7.5, more preferably 5.5~7.0. Ammonia water, calcium carbonate, urea and so forth can be used as the neutralization reagent. The cultivation is carried out at a temperature of 25~55° C.

The difference between the rate of lactic acid production and the rate of lactic acid consumption is determined as the accumulated concentration of lactic acid, which should preferably be controlled to be not more than 1.5% (wt/vol), more preferably not more than 1.0% (wt/vol); in other words, it is important to minimize the accumulated amount of lactic acid. When an amino acid-producing microorganism having a high ability to assimilate lactic acid is employed, the lactic acid concentration is observed to be kept at a value of a negligible order even without any special control. The control of the concentration of lactic acid is carried out by regulating the cultivation temperature, the pH of the culture medium, the rate of oxygen supply to the culture medium upon measurement of the lactic acid concentration in the medium (for example, lactate dehydrogenase is used for the measurement). For instance, an elevation of the value of the pH to a range from slight acidity to weak alkalinity lowers the rate of the lactic acid fermentation and hence the lactic acid concentration; further, an increase in oxygen supply lowers the lactic acid concentration.

After completion of the cultivation, the resulting culture broth is heated at a temperature of 75~100° C.; the heat treatment coagulates heat-coagulating proteins and facilitate the separation of microbial cells. Microbial cells and heat-coagulating proteins; etc. are removed by filtration or centrifugation.

An amino acid present in the broth is determined by microbiological assay methods or colorimetric methods based on a ninhydrin reaction.

An amino acid can be isolated according to the ordinary procedures from the filtrate or supernatant solution.

To further illustrate the present invention, and not by way of limitation, the following examples are given.

EXAMPLE 1

*Lactobacillus bulgaricus* (IFO-3533) and *Streptococcus thermophilus* (IFO-3535) were each inoculated from each stabcultures in an agar medium into each 10 ml of a medium (Medium A) having the following composition:

| Medium A (for seed culture) | |
|---|---|
| | g/l |
| Glucose | 10 |
| Peptone | 12.5 |
| Yeast extracts | 7.5 |
| $KH_2PO_4$ | 5.0 |
| $MgSO_4.7H_2O$ | 0.8 |
| NaCl | 5.0 |
| $MnCl_2.4H_2O$ | 0.14 |
| $FeSO_4.7H_2O$ | 0.04 |
| $Na_2CO_3$ | 1.25 |
| Tween 80 | 0.2 |
| pH—6.8 (after sterilization at 120° C. for 15 min) | |

The two inocula were each incubated at 37° C. for 20 hours. Three milliliters of the each inocula was added to 100 mls of the second medium (Medium B) having the following composition:

| Medium B (for seed culture) | |
|---|---|
| | g/l |
| Cheese whey (as lactose) | 30 |
| $KH_2PO_4$ | 1 |
| Yeast extracts | 6 |
| $MgSO_4.7H_2O$ | 0.5 |
| $CaCO_3$ | 30 |
| pH—6.5 (after sterilization at 120° C. for 15 min) | |

Stationary culture for lactic acid fermentation was conducted at 37° C. for 24 hours. The resulting culture was used as an inoculum (Seed A) for a mixed culture with amino acid-producing microorganisms listed in Table 1.

The amino acid-producing microorganisms were each inoculated from an agar slant into 5 ml of a medium (Medium C) having the following composition:

| Medium C (for seed culture) | |
|---|---|
| | g/l |
| Glucose | 10 |
| Peptone | 10 |
| Meat extracts | 5 |
| NaCl | 5 |
| Lactate* | 3~5 |
| pH—7.0 (after sterilization at 120° C. for 15 min) | |

*Culture broth obtained by cultivating *Sc. thermophilus* plus *L. bulgaricus* in a medium (Medium B, lactose 40~50 g/l) at 37° C. for 72 hr was used as the source of lactic acid.

Aerobic shaking was conducted at 30° C. for 20 hr. One milliliter of the resulting culture was then inoculated into 20 ml of a fermentation medium (D) having the following composition:

| Medium D (for fermentation) | g/l |
|---|---|
| Cheese whey (as lactose) | 50 |
| Glucose | 10 |
| KH$_2$PO$_4$ | 0.5 |
| K$_2$HPO$_4$ | 0.5 |
| MgSO$_4$.7H$_2$O | 0.5 |
| FeSO$_4$.7H$_2$O | 0.02 |
| MnSO$_4$.4H$_2$O | 0.01 |
| ZnSO$_4$.7H$_2$O | 0.01 |
| (NH$_4$)$_2$SO$_4$ | 25 |
| CaCO$_3$ (sterilized separately) | 50 |
| Initial pH 6.7 for bacterial strains | |
| 6.0 for yeast strains | |

Fermentation was carried out by culturing at 30° C. with aerobic shaking for 16 hr, and then 3% by volume of the inoculum of lactic acid microorganisms (Seed A) was inoculated into the fermentation medium.

Fermentation was continued with aerobic shaking at 30° C. for further 60 hr. The pH of the medium was adjusted to 4.5~6.5 for yeast strains and 5.0~7.0 for bacterial strains with a caustic soda or hydrochloric acid solution during cultivation. Upon completion of cultivation, the resulting culture broth was heated at 95° C. for 5 min. This procedure renders microbial cells and precipitates such as heat-coagulating proteins readily removable by centrifugation or filtration.

TABLE 1

Amino Acids Fermentation Using Whey

| Microorganisms | Assimilability* Lactic acid, | Lactose | Mixed culture Cell growth** | Amino acids | Monoculture Cell growth** | Amino acids |
|---|---|---|---|---|---|---|
| Alkaligenes faecalis IFO-3160 | + | − | 7.5g/l L-Lys<br>L-Val<br>L-Ileu | 250mg/l<br>200mg/l<br>400mg/l | 1.5g/l | less than 100mg/l |
| Acinetobacter 38-15 FERM-P-2188 (S—AEC resistant) | + | − | 10g/l L-Lys<br>L-Val<br>L-Ileu<br>L-Leu | 4500mg/l<br>300mg/l<br>200mg/l<br>100mg/l | negligible | less than 100mg/l |
| Arthrobacter No. 18 FERM-P-1481 (threonine resistant) | + | − | 8g/l L-Lys<br>L-Val<br>L-Ileu | 1200mg/l<br>200mg/l<br>500mg/l | negligible | less than 100mg/l |
| Bacillus circulans IFO-3329 | + | ± | 7g/l L-Lys | 350mg/l | 3g/l | less than 100mg/l |
| Bacillus subtilis IAM-1071 | + | − | 6.5g/l L-Lys<br>L-Glu<br>DL-Ala<br>L-Val | 150mg/l<br>500mg/l<br>400mg/l<br>200mg/l | 1.5g/l | less than 100mg/l |
| Brevibacterium alkanolyticum IFO-12922 | + | − | 12g/l L-Lys<br>L-Glu<br>L-Val | 200mg/l<br>2500mg/l<br>300mg/l | negligible | less than 100mg/l |
| Brevibacterium flavum ATCC-13826 | + | − | 10g/l L-Glu<br>L-Lys<br>L-Val<br>DL-Ala<br>L-Leu<br>L-Ileu<br>Glycine | 1500mg/l<br>450mg/l<br>600mg/l<br>300mg/l<br>200mg/l<br>150mg/l<br>200mg/l | 2.5g/l L-Glu<br>L-Val | 300mg/l<br>150mg/l |
| Brevibacterium lactofermentum ATCC-21420 (Tyrosine-auxotroph) | + | − | 9.5g/l L-Glu<br>DL-Ala<br>L-Val<br>L-Ileu<br>L-Phe<br>L-Lys | 500mg/l<br>2500mg/l<br>800mg/l<br>300mg/l<br>500mg/l<br>700mg/l | 2.0g/l L-Glu<br>DL-Ala | 200<br>300 |
| Corynebacterium hydrocarboclastum ATCC-15592 | + | − | 11g/l L-Glu<br>L-Lys | 1500mg/l<br>150mg/l | negligible | less than 100mg/l |
| Corynebacterium acetoacidophilum ATCC-13870 | + | − | 8g/l DL-Ala<br>L-Val<br>L-Ileu | 500mg/l<br>200mg/l<br>150mg/l | 1.5g/l | less than 100mg/l |
| Flavobacterium lutescens IFO-3085 | + | − | 7g/l L-Lys | 250mg/l | 2.0g/l | less than 100mg/l |
| Micrococcus roseus IFO-3768 | + | − | 9g/l L-Lys<br>L-Val<br>L-Ileu | 200mg/l<br>200mg/l<br>300mg/l | 1.5g/l | less than 100mg/l |
| Nocardia erythropolis IAM-12122 | + | − | 12g/l L-Glu<br>L-Lys | 2500mg/l<br>150mg/l | negligible | less than 100mg/l |
| Serratia plymuthicum IFO-3055 | + | ± | 10g/l L-Lys<br>DL-Ala | 150mg/l<br>400mg/l | 3.0g/l | less than 100mg/l |
| Proteus morganii IFO-3848 | + | − | 8g/l L-Lys<br>L-Val | 250mg/l<br>200mg/l | 2.0g/l | less than 100mg/l |
| Saccharomyces cerevisiae IFO-0971 | + | − | 8.5g/l DL-Ala<br>L-Glu<br>L-Asp | 500mg/l<br>500mg/l<br>300mg/l | 3g/l | less than 100mg/l |
| Saccharomyces oviformis | + | − | 12g/l DL-Ala | 2500mg/l | 3.5g/l | less than |

TABLE 1-continued

Amino Acids Fermentation Using Whey

| Microorganisms | Assimilability* | | Mixed culture | | Monoculture | |
|---|---|---|---|---|---|---|
| | Lactic acid | Lactose | Cell growth** | Amino acids | Cell growth** | Amino acids |
| IAM-4325 | | | L-Glu | 1000mg/l | | 100mg/l |
| | | | L-Val | 200mg/l | | |
| *Sporoboromyces roseus* IFO-1037 | + | − | 10g/l DL-Ala | 1500mg/l | 3.5g/l | less than 100mg/l |
| | | | L-Glu | 500mg/l | | |
| *Candida humicola* IFO-1577 | + | ± | 15g/l DL-Ala | 500mg/l | 8g/l L-Glu | 800mg/l |
| | | | L-Glu | 1500mg/l | L-Asp | 300mg/l |
| | | | L-Val | 200mg/l | | |
| | | | L-Asp | 500mg/l | | |
| *Schizosaccharomyces pombe* IFO-6170 | + | − | 8g/l DL-Ala | 500mg/l | 3g/l | less than 100mg/l |
| | | | L-Glu | 1500mg/l | | |

*Note 1 Assimilability
+: assimilable, ±: weakly assimilable, −: nonassimilable
**Note 2 Cell growth
An increase in the weight of precipitates (dried weight) in the broth after dissolving calcium carbonate by addition of hydrochloric acid is regarded as an indicator of the cell growth.
Note 3 Abbreviation of amino acids:
Lys: Lysine, Val: Valine, Ileu: Isoleucine, Glu: Glutamate, Leu: Leucine, Phe: Phenylalanine, Ala: Alanine, Asp: Aspartic acid

EXAMPLE 2

*Brevibacterium flavum* (ATCC-13326), *Corynebacterium glutamicum* (ATCC-13032), *Micrococcus lysodeikticus* (IAM-3333), *Micrococcus roseus* (IFO-3768), *Brevibacterium lactofermentum* (ATCC-13869), *Brevibacterium linens* (IFO-12142), and *Microbacterium ammoniafilm* (ATCC-15354) were each cultivated in the same manner as Example 1, except that 4 I.U. per milliliter of potassium salt of penicillin G was added 16 hr after the start of cultivation, together with lactic acid microorganisms employed in Example 1 and the pH of the medium was adjusted to 6.0~7.0. It was confirmed that the lactic acid bacteria employed were resistant to 5 I.U./ml of Penicillin G under the present culture conditions. The amounts of L-glutamic acid accumulated in the culture broth after 3 days of cultivation are shown in Table 2.

TABLE 2

| Microorganisms | L-Glutamic acid accumulated g/l |
|---|---|
| *Brevibacterium flavum* ATCC-13326 | 18.0 |
| *Corynebacterium glutamicum* ATCC-13032 | 17.0 |
| *Micrococcus roseus* IFO-3768 | 8.5 |
| *Brevibacterium lactofermentum* ATCC-13869 | 15.0 |
| *Brevibacterium linens* IFO-12142 | 6.0 |
| *Microbacterium ammoniafilm* ATCC-15354 | 14.0 |
| *Micrococcus lysodeikticus* IAM-3333 | 5.0 |

EXAMPLE 3

An L-lysine-producing strain, *Brevibacterium flavum* (ATCC-13326, homoserine-requiring) mutationally derived from the parent strain, *Brev. flavum* (ATCC-13826) was incubated with aerobic shaking in 30 ml of a medium (Medium C in Example 1) at 30° C. for 24 hr.

Three milliliters of the resulting culture broth and 0.5 ml of an inoculum of a lactic acid bacteria (Seed A in Example 1) were inoculated into 27 ml of fermentation medium (Medium E) having the following composition:

| Medium E (for fermentation) | |
|---|---|
| | g/l |
| Cheese whey (as lactose) | 80 |
| Glucose | 20 |
| $KH_2PO_4$ | 0.5 |
| $K_2HPO_4$ | 0.5 |
| $MgSO_4.7H_2O$ | 0.5 |
| $FeSO_4.7H_2O$ | 0.02 |
| $ZnSO_4.7H_2O$ | 0.01 |
| $MnSO_4.7H_2O$ | 0.01 |
| $(NH_4)_2SO_4$ | 35 |
| C.S.L. | 7.5 |
| $CaCO_3$ | 50 |
| L-homoserine | 0.2 |

The pH was adjusted to 6.7 after sterilization at 120° C. for 15 min.

Mixed-cultivation was conducted in the same manner as in Example 1. After 72 hours of cultivation, the concentration of L-lysine in the resulting culture broth was 24.5 g/l (as the hydrochloride). Five grams of L-valine per liter was also found in the culture broth.

EXAMPLE 4

Mixed-cultivation was carried out by each employing, as an amino acid-producing microorganism, *Corynebacterium acetoacidophilum* (ATCC-21476, homoserine-requiring), and *Corynebacterium glutamicum* (ATCC-13287, homoserine-requiring) in the same manner as in Example 3. After 3 days of cultivation, the amount of L-lysine produced was 22.0 and 12.0 g/l, respectively.

EXAMPLE 5

Mixed-cultivation was carried out by employing *Brevibacterium lactofermentum* (FERM-P-1945, 2-thiazolealanine-resistant) as an amino acid-producing microorganism in the same manner as in Example 3, except that L-homoserine in Medium E was omitted. After 4 days of cultivation, the amount of L-valine produced was 12 g/l. On the other hand, in the case of mono-culture using the same strain as an amino acid-producing microorganism, the amount of L-valine produced was 1.5 g/l.

EXAMPLE 6

Mixed-cultivation was carried out by each employing, as an L-threonine-producing microorganism an L-isoleucine-requiring mutant (ATCC-19560) derived from *Corynebacterium hydrocarboclastum* (ATCC-15592) and an L-threonine analogue-resistant mutant (ATCC-21269) derived from *Brevibacterium flavum* (ATCC-13826) in the same manner as in Example 1, except that *Streptococcus cremoris* (IFO-3427) was employed as a lactic acid microorganism in place of Sc. thermophilus and 100 mg/l of L-isoleucine was added to the fermentation medium. L-threonine produced after 3 days of cultivation was 1.2 g/l and 3.2 g/l, respectively.

EXAMPLE 7

*Nocardia alkanoglutinosa* No. 223-59 (ATCC-31220, S-AEC-resistant) was employed as an L-lysine-producing strain. The strain was obtained by mutational treatment from a hydrocarbon-assimilating strain isolated from soil (U.S. Pat. No. 4,123,329). The strain can utilize hydrocarbon, lactic acid, pyruvic acid, or acetic acid but not lactose or sucrose as a sole carbon source. The assimilability of glucose is weak. The strain was inoculated from an agar slant into 50 ml of a medium (Medium E) having the following composition:

| Medium E (For seed culture) | |
|---|---|
| | g/l |
| Fructose | 15 |
| Peptone | 5 |
| $(NH_4)_2SO_4$ | 4 |
| NaCl | 1 |
| $K_2HPO_4$ | 1 |
| $KH_2PO_4$ | 1 |
| $MgSO_4.7H_2O$ | 0.5 |
| $FeSO_4.7H_2O$ | 0.02 |
| $MnSO_4.4H_2O$ | 0.01 |
| $ZnSO_4.7H_2O$ | 0.01 |
| Lactic acid* | 6~7 |
| pH | 6.7 |

*The same culture broth as in Medium C in Example 1 was used.

Cultivation was conducted with aerobic shaking at 30° C. for 24 hr.

On the other hand, an inoculum of Lactobacillus bulgaricus was prepared using the culture media A and B in the same manner as in Example 1.

One milliliter of each inoculum was inoculated into a fermentation medium (Medium F) having the following composition:

| Medium F (for fermentation) | |
|---|---|
| | g/l |
| Glucose | 100 |
| $KH_2PO_4$ | 0.5 |
| $K_2HPO_4$ | 0.5 |
| $MgSO_4.7H_2O$ | 0.5 |
| NaCl | 1 |
| $FeSO_4.7H_2O$ | 0.02 |
| $MnSO_4.4H_2O$ | 0.01 |
| $ZnSO_4.7H_2O$ | 0.01 |
| $(NH_4)_2SO_4$ | 35 |
| Peptone | 5 |
| $CaCO_3$ | 50 |

The pH was adjusted to 6.7~6.8 after sterilization at 120° C. for 15 min.

The mixed-cultivation was carried out with aerobic shaking at 30° C. for 4 days.

In a control experiment, only an inoculum of *Nocardia alkanoglutinosa* ATCC-31220 was inoculated into Medium F and mono-culture was carried out at 33° C. with shaking for 4 days.

Accumulated amounts of L-lysine were 14.8 g/l and 2.1 g/l, respectively, with mixed-cultivation and the mono-culture.

EXAMPLE 8

Mixed-cultivation was carried out by using various strains of lactic acid microorganisms in the same manner as in Example 7. The results are shown in Table 2.

TABLE 2

| Strains (Monoculture) | | L-lysine HCl 2.2 g/l |
|---|---|---|
| (Mixed culture) | | |
| Lactobacillus acidophilus | IFO-3532 | 14.2 |
| Lactobacillus casei | IFO-12004 | 10.5 |
| Lactobacillus thermophilus | IFO-3863 | 8.5 |
| Lactobacillus delbrueckii | IFO-3534 | 4.1 |
| Lactobacillus plantarum | IFO-12006 | 8.1 |
| Streptococcus cremoris | IFO-3427 | 14.5 |
| Streptococcus thermophilus | IFO-3535 | 14.1 |
| Leuconostoc dextranicum | IFO-3347 | 4.1 |
| Leuconostoc mesenteroides | IFO-3426 | 3.5 |
| Bacillus coagulans | IFO-3887 | 3.5 |
| Pediococcus soyae | IFO-12172 | 8.0 |
| Pediococcus pentosaseus | IFO-3891 | 4.5 |
| Rhizopus oryzae | IFO-4706 | 7.5 |

EXAMPLE 9

*Lactobacillus delbrueckii* (IFO-3534) and *Streptococcus thermophilus* (IFO-3535) were each inoculated into a medium (Medium A), and the inocula were each incubated at 37° C. for 20 hr. Three milliliters of each inoculum was added to 100 ml of a culture medium containing 2.5 g/dl cane molasses (as sugar), 0.1 g/dl $KH_2PO_4$, 0.05 g/dl $MgSO_4.7H_2O$, 0.5 g/dl yeast extract, 0.5 g/dl peptone, and 3 g/dl $CaCO_3$, and having an initial pH of 6.8. Cultivation was conducted at 37° C. for 24 hr.

On the other hand, an inoculum of an L-lysine-producing strain, *Nocardia alkanoglutinosa*(FERM-P-6046) was prepared according to a procedure in Example 7.

Two milliliters of the inoculum thus obtained and 0.5 ml of the inoculum of lactic acid bacteria described above were inoculated into 28 ml of a fermentation medium containing 8 g/dl (as sugar) can molasses, 2 g/dl (as lactose) cheese whey, 0.05 g/dl $K_2HPO_4$, 0.05 g/dl $KH_2PO_4$, 0.05 g/dl $MgSO_4.7H_2O$, 1.0 g/dl C.S.L., 0.2 g/dl casein hydrolysates, 3.5 g/dl $(NH_4)_2SO_4$, and 5.0 g/dl $CaCO_3$ and having an initial pH of 6.8.

Mixed-cultivation was conducted with aerobic shaking at 34~35° C. for 94 hr. The amount of L-lysine produced was 26.5 g/l (as the hydrochloride).

EXAMPLE 10

*Lactobacillus bulgaricus* IFO-3533 and *Streptococcus thermophilus* IFO-3535 (the inoculation ratio: 1:1) were inoculated into 100 ml of Medium A and cultured at 37° C. overnight. Microbial cells were harvested by centrifugation, washed with sterilized saline water, and suspended in 10 ml of sterilized saline water. The cell suspension was mixed with 20 ml of sterilized solution of 3 g/dl of sodium alginate (a gel-inducing reagent).

The suspension was then poured by drops into a 2% by weight in volume solution of $CaCl_2$. Beads formed were washed with sterilized saline solution.

Two milliliters of an inoculum of *Nocardia alkanoglutinosa* 223-59 obtained by the same procedure described in Example 7 was inoculated into 30 ml of a fermentation medium (Medium D) containing cheese whey and glucose.

About 20 droplets of the beads obtained above in which cells of the lactic acid microorganism had been immobilized were placed aseptically into the fermentation medium.

Mixed-cultivation was carried out at 33° C. for 70 hr. The pH of the culture medium was held at 6.0~6.8 during the cultivation. The amount of L-lysine produced after 3 days' cultivation was 8.5 g/l (as the hydrochloride).

EXAMPLE 11

L-lysine production from whey permeate was conducted in a 2-l jar fermentor. The whey sample was a product obtained by ultrafiltration of cheese whey (the dried sample contains 84% of lactose and 9% of ash).

An inoculum of *Nocardia alkanoglutinosa*(FERM-P-6064) was prepared by the same procedure as in Example 7. Fifty milliliters of the inoculum, together with 30 ml of the inoculum of *L. bulgaricus* plus *Sc. thermophilus* (Seed A in Example 1), was inoculated into 1,000 ml of a fermentation medium of the following composition: 10 g/dl (as lactose) cheese whey permeate, 0.4 g/dl ethyl alcohol, 0.05 g/dl $K_2HPO_4$, 0.05 g/dl $KH_2PO_4$, 0.05 g/dl $MgSO_4.7H_2O$, 0.5 g/dl C.S.L., 0.5 g/dl peptone, 0.2 g/dl casein hydrolysates, 1.75 g/dl $(NH_4)_2SO_4$, with an initial pH of 6.8.

The mixed-cultivation was conducted with stirring (1,000 r.p.m.) and aeration (1.0 V.V.M.). The pH of the medium was held at pH 6.6~6.8 for 24 hr from the start of the cultivation with sulfuric acid and thereafter adjusted to 6.0~6.2 with ammonia water. During the cultivation, the content of lactic acid in the culture medium was determined by an enzymatic method using lactate dehydrogenase.

At the initial stage of the cultivation, the concentration of L-lactic acid increased up to 0.5 g/dl (12 hours of the cultivation) and thereafter decreased rapidly down to less than 0.1 g/dl. The amount of L-lysine produced after 50 hours of the cultivation was 30.5 g/l (as the hydrochloride).

The culture broth was heated at 95° C. for 15 min to give 21 g of dried cells from 1 liter of the culture broth.

The L-lysine was separated and purified from the filtrate by a conventional method using an ion-exchange resin to yield 11.5 g of L-lysine hydrochloride from 500 ml of the filtrate.

EXAMPLE 12

Two milliliters of an inoculum of *Nocardia alkanoglutinosa* (FERM-P-6064) prepared by the same procedure as in Example 7 and 0.5 ml of an inoculum of *L. bulgaricus* plus *Sc. thermophilus* (Seed A) described in Example 1 were inoculated into a medium containing 10 g/dl solution starch, 3.5 g/dl $(NH_4)_2SO_4$, 0.05 g/dl $KH_2PO_4$, 0.05 g/dl $K_2HPO_4$, 0.05 g/dl $MgSO_4.7H_2O$, 2 mg/dl $FeSO_4.7H_2O$, 1 mg/dl $MnSO_4.4H_2O$, 1 mg/dl $ZnSO_4.7H_2O$, 0.3 g/dl casein hydrolysates, 0.4 g/dl peptone, and 5 g/dl $CaCO_3$ and having an initial pH of 6.8.

Before the start of the cultivation, 5 units per gram starch of glucoamylase (one unit: the amount which yield 10 mg of glucose by a reaction at 40° C., pH 4.5, for 30 min) was added aseptically to the fermentation medium. A filtrate [with a membrane filter (Millipore filter; pore size 0.22µ)] of glucoamylase was used.

Mixed-cultivation was conducted with aerobic shaking at 35° C. for 90 hr. The amount of L-lysine produced was 25.0 g/l (as the hydrochloride).

What is claimed is:

1. In a process for producing an amino acid by mixed-cultivating microorganisms in an aqueous nutrient medium containing one or more carbohydrates, accumulating an amino acid in the resultant culture broth, and recovering the amino acid from the culture broth, the improvement comprising aerobically mixed-cultivating an amino acid-producing microorganism having an ability of assimilating lactic acid, but having no or a weak ability of assimilating at least one carbohydrate in the nutrient medium, and at least one lactic acid-producing microorganism having an ability of assimilating the carbohydrate which is nonassimilable or weakly assimilable by said amino acid-producing microorganism, whereby an amino acid is produced from the carbohydrate in one step operation.

2. The process according to claim 1 wherein the amino acid is a member selected from the group consisting of L-lysine, L-valine, L-threonine, L-glutamic acid, L-isoleucine, L-leucine, DL-alanine, L-phenylalanine, L-tyrosine, L-tryptophane, L-arginine, L-histidine, L-serine, L-glycine, and L-aspartic acid.

3. The process according to claim 1 wherein the amino acid-producing microorganism is a member belonging to a genus selected from the group consisting of Alkaligenus, Acinetobacter, Arthrobacter, Bacillus, Brevibacterium, Corynebacterium, Flavobacterium, Micrococcus, Microbacterium, Nocardia, Proteus, Serratia, Candida, Saccharomyces, Sporoboromyces, and Schizosaccharomyces.

4. The process according to claim 3 wherein the amino acid-producing microorganism is a member selected from the group consisting of the species *Alkaligenes faecalis, Alkaligenes marshallii, Acinetobacter sp-38-15, Acinetobacter calcoaceticus, Arthrobacter paraffineus, Arthrobacter citreus, Arthrobacter sp-18, Bacillus circulans, Bacillu megatherium, Bacillus subtilis, Brevibacterium ammoniagenes, Brevibacterium acetylicum, Brevibacterium thiogenitalis, Brevibacterium flavum, Brevibacterium lactofermentum, Corynebacterium hydrocarboclastum, Corynebacterium acetoacidophilum, Corynebacterium glutamicum, Flavobacterium lutescens, Micrococcus luteus, Micrococcus roseus, Microbacterium ammoniafilm, Nocardia alkanoglutinosa, Nocardia erythropolis, Nocardia lyena, Proteus morganii, Serratia marcescens, Serratia plymuthicum, Saccharomyces cerevisiae, Saccharomyces oviformis, Candida humicola, Candida lypolitica, Sporoboromyces roseus, Schizosaccharomyces pombe.*

5. The process according to claim 1 wherein the lactic acid microorganism is a member belonging to a genus selected from the group consisting of Lactobacillus, Streptococcus, Leuconostoc, Pediococcus, Tetracoccus, Bacillus, and Rhizopus.

6. The process according to claim 5 wherein the lactic acid microorganism is a member selected from the group consisting of the species *Lactobacillus bulgaricus, Lactobacillus casei, Lactobacillus acidophilus, Lactobacillus japonicus, Lactobacillus thermophilus, Lactobacillus*

*plantarum, Lactobacillus delbrueckii, Lactobacillus pentosus, Streptococcus cremoris, Streptococcus thermophilus, Streptococcus lactis, Leuconostoc dextranicum, Pediococcus acidilactici, Pediococcus pentosaceus, Pediococcus soyae, Tetracoccus soyae, Bacillus coagulans, Bacillus laevolactici,* and *Rhizopus oryzae*.

7. The process according to claim 1, claim 5, or claim 6 wherein the lactic acid microorganism is living cells immobilized in or on a supporting material.

8. The process according to claim 1, claim 5, or claim 6 wherein the lactic acid microorganism is a mutant strain resistant to antibiotics or amino acid analogues.

9. The process according to claim 1 wherein the carbohydrate is a member selected from the group consisting of glucose, fructose, sucrose, molasses, starch hydrolysates, cellulose hydrolysates, hydrol, lactose, lactose hydrolysates, fruit juice, casein whey, cheese whey, soybean whey, dextrin, and starch.

10. The process according to claim 1 wehrein the mixed-cultivation is carried out by inoculating a seed culture obtained by cultivating the amino acid-producing microorganism in an aqueous nutrient medium containing lactic acid, its salt, or a culture broth of the lactic acid microorganism, into the aqueous nutrient medium for amino acid production.

11. The process according to claim 1 wherein the mixed cultivation is carried out by inoculating the amino acid-producing microorganism into the aqueous nutrient medium for amino acid production containing lactic acid followed by precultivating the microorganism before inoculation of the lactic acid microorganism into the aqueous nutrient medium.

12. The process according to claim 1 wherein the mixed-cultivation is carried out by inoculating a seed culture obtained by aerobically cultivating both the amino acid-producing microorganism and the lactic acid microorganism in an aqueous nutrient medium containing the carbohydrate, into the aqueous nutrient medium for amino acid production.

13. The process according to claim 1 or claim 12 wherein the mixed-cultivation is carried out by maintaining the concentration of lactic acid accumulated in the culture medium during the cultivation, in the range of not more than 1.5% by weight/volume.

14. The process according to claim 13 wherein the control of the concentration of lactic acid is maintained in the range of not more than 1.5% by regulating the cultivation temperature, the pH of the culture medium, the rate of oxygen supply to the culture medium, or a combination of these.

15. The process according to claim 1 wherein the cultivation is carried out at a pH of 4.5~7.5.

16. The process according to claim 1 wherein the cultivation is carried out at a temperature of 25°~55° C.

17. The process according to claim 1 wherein the carbohydrate is starch or dextrine and amylase is added to the aqueous nutrient medium.

18. The process according to claim 1 wherein the lactic acid microorganism is one producing an antimicrobial substance and the amino acid-producing microorganism is a mutant strain resistant to the antimicrobial substance.

* * * * *